(12) United States Patent
Haase et al.

(10) Patent No.: US 8,348,909 B2
(45) Date of Patent: Jan. 8, 2013

(54) IMPLANTABLE THERAPEUTIC SUBSTANCE DELIVERY DEVICE WITH SEPTUM GUIDE AND METHOD OF USE

(75) Inventors: James M. Haase, Maplewood, MN (US); Wende L. Dewing, Edina, MN (US); William K. Wenger, St. Paul, MN (US); Beth Bullemer, Maple Plain, MN (US)

(73) Assignee: Medtronic, Inc., Minneapolis, MN (US)

( * ) Notice: Subject to any disclaimer, the term of this patent is extended or adjusted under 35 U.S.C. 154(b) by 1471 days.

(21) Appl. No.: 11/413,313

(22) Filed: Apr. 28, 2006

(65) Prior Publication Data

US 2007/0255234 A1    Nov. 1, 2007

(51) Int. Cl.
*A61M 31/00* (2006.01)
(52) U.S. Cl. .................. 604/288.01; 604/892.1
(58) Field of Classification Search .... 604/890.1–892.1, 604/65–67, 131–139, 288.01–288.04
See application file for complete search history.

(56) References Cited

U.S. PATENT DOCUMENTS

| | | | |
|---|---|---|---|
| 4,286,584 A | 9/1981 | Sampson et al. | |
| 4,573,994 A | 3/1986 | Fischell et al. | |
| 4,760,837 A | 8/1988 | Petit | |
| 5,360,407 A | 11/1994 | Leonard et al. | |
| 5,741,228 A | 4/1998 | Lambrecht et al. | |
| 5,848,989 A | 12/1998 | Villani | |
| 6,293,922 B1 | 9/2001 | Haase | |
| 6,428,504 B1 | 8/2002 | Riaziat et al. | |
| 6,582,418 B1 * | 6/2003 | Verbeek et al. | 604/892.1 |
| 6,592,571 B1 | 7/2003 | Verbeek et al. | |
| 6,689,142 B1 | 2/2004 | Tremaglio, Jr. et al. | |
| 7,785,302 B2 * | 8/2010 | Powers | 604/288.02 |
| 2001/0037094 A1 | 11/2001 | Adaniya et al. | |
| 2004/0078000 A1 | 4/2004 | Borchard et al. | |
| 2004/0199220 A1 | 10/2004 | Cantlon | |

OTHER PUBLICATIONS

PCT Search Report mailed Nov. 13, 2007; 13 pgs.

* cited by examiner

*Primary Examiner* — Kevin C Sirmons
*Assistant Examiner* — Phillip Gray

(57) ABSTRACT

An implantable delivery device including a housing, a port assembly, and a plurality of grooves. The housing includes an outer wall defining an exterior face. The port assembly includes a septum and a port opening that is exteriorly open relative to the housing face. The plurality of grooves are formed in the exterior face proximate the port opening, and are sized to receive a needle tip to guide the needle tip toward the port opening. In one embodiment, the port assembly is fluidly connected to a reservoir, such that the port assembly constitutes a reservoir refill port.

17 Claims, 7 Drawing Sheets

IMPLANTABLE THERAPEUTIC SUBSTANCE DELIVERY DEVICE WITH SEPTUM GUIDE AND METHOD OF USE

BACKGROUND OF THE INVENTION

The present invention relates to implantable medical devices for delivering a liquid therapeutic substance to a delivery site within a patient. More particularly, it relates to systems and methods for guiding a hypodermic needle tip toward a septum opening associated with an implantable therapeutic substance delivery device.

A variety of implantable medical devices are available for treating patients. For example, implantable therapeutic substance delivery devices are typically used to deliver infusion media or therapeutic substance (such as medication) to a patient at a regulated dosage. The implantable therapeutic substance delivery device (sometimes referred to as a drug pump or medicament pump) is implanted by a clinician into a patient at a location appropriate for the therapy. Typically, an infusion catheter is connected to an outlet of the device and is implanted/positioned to infuse the therapeutic substance at the desired therapy site so as to treat a condition such as pain, spasticity, cancer, neurodegenerative disease, trauma, or other medical condition. The term "implantable therapeutic substance delivery device" as used herein, refers to any device for delivering medicaments including, but not limited to, bladder pumps, accumulator pumps, fixed-rate bellows pumps, and the like, as well as implantable delivery devices that do not include a pump.

In general terms, the implantable therapeutic substance delivery device commonly includes a drug reservoir containing a volume of the infusion media along with a pumping and/or metering mechanism to propel the infusion media in some metered or constant flow dosage to the desired location from the reservoir via the catheter. Over time, the reservoir becomes depleted and it is necessary to refill the device with a new supply of the therapeutic substance. In order to avoid the need for surgery to access and refill the device, it is desirable to have the ability to percutaneously refill the drug reservoir. This is commonly achieved by providing the delivery device with a reservoir refill port that otherwise includes a resilient, resealable septum. The refill port is percutaneously accessible by introducing a hypodermic needle through the skin and into the refill port, and then through the septum, thereby forming a fluid connection between the needle and the drug reservoir. Additional septum-type ports can also be provided, such as a catheter access port. The catheter access port is also accessible percutaneously via hypodermic needle, and provides direct access to the catheter, bypassing the pumping/metering mechanism to allow the infusion of media directly into the patient, or removal of fluid from the patient (e.g., cerebral spinal fluid), via the catheter.

Percutaneously accessing the septum with a hypodermic needle can be difficult. One well-accepted approach entails the clinician using his/her fingers to palpate the device's periphery through the patient's skin. Once generally located, the clinician then searches/palpates for the desired port, again using his/her fingers. Port location relative to a perimeter or outline of the device is normally generally known to the clinician, as he or she will have a working understanding of the device's footprint and port location(s) relative thereto. In this regard, a template can be employed that can otherwise provide an external visual map of port location when properly arranged on the patient's skin. In general terms, once the device's general location and orientation is ascertained, the template is placed onto the patient's skin in general alignment with the estimated implanted device location and orientation. The template includes a representation of the port location(s), thus giving the clinician visual guidance.

Regardless of how the clinician initially estimates port location, a hypodermic needle is then pierced through the patient's skin. While the clinician's initial estimate of the port location is in many instances correct, on occasion the hypodermic needle may not impinge directly into the port/septum. For example, where the patient's skin is relatively thick, it may be difficult for the clinician to accurately estimate port location and/or the clinician may simply be offline from the anticipated target. Regardless, where the hypodermic needle does not immediately enter the port with initial insertion, the clinician will tactilely sense a hard stop to forward movement of the hypodermic needle (i.e., as the needle tip contacts the rigid housing of the device) as compared to a more subtle resistance to needle advancement when piercing through the septum.

Upon determining that the hypodermic needle is not within the port, the clinician can remove the needle and then make another insertion attempt. In many instances, however, the clinician will be of the mind set that his/her initial estimate of the port/septum location is approximately correct, that the needle was introduced in-line with this estimation, and thus that the needle tip must be in close proximity to the actual port opening. As a result, instead of removing the needle and re-attempting the percutaneous insertion, the clinician will oftentimes drag the needle tip along the contacted face of the device, searching for the port opening. While viable, this technique can be time consuming as the clinician may inadvertently move the needle tip in a direction that is actually away from the port opening, and can be source of discomfort for the patient.

In light of the above, some efforts have been made to enhance the clinician's ability to better estimate port location prior to piercing the needle through the patient's skin. The above-described device template is one example. Other, more complex devices have also been suggested, such as electronically sensing the port opening location, employing sensors that detect the presence of the needle relative to a port opening, etc. While potentially viable, these techniques entail additional costs and clinician training. Further, even with these devices in place, the opportunity for misalignment of the needle tip relative to the port opening with initial insertion still remains.

In light of the above, a need exists for a system and method for guiding a misaligned needle tip toward a septum port associated with an implantable therapeutic substance delivery device.

SUMMARY OF THE INVENTION

Some aspects in accordance with principles of the present invention relate to an implantable therapeutic substance delivery device for delivering a liquid therapeutic substance to a delivery site within a patient. The device includes a housing, a port assembly, and a plurality of grooves. The housing includes an outer wall defining an exterior face. The port assembly includes a port passage and a septum. The port passage terminates at a port opening that is exteriorly open relative to the exterior face. The septum is disposed across the port passage. Finally, the plurality of grooves are formed in the exterior face proximate the port opening such that the grooves are opened relative to an exterior of the device. Further, each of the grooves are sized to receive a needle tip. With this configuration, each of the grooves are adapted to guide a needle tip positioned therein toward the port opening. In one embodiment, the port passage is fluidly connected to a reservoir maintained by the housing, such that the port assembly constitutes a drug refill port assembly. In other embodiments, each of the plurality of grooves are linear, extending in a generally radial fashion relative to a center point of the port opening.

Other aspects in accordance with principles of the present invention relate to a method of percutaneously delivering a hypodermic needle to a septum within a port assembly passage of a human implantable therapeutic substance delivery device. The device includes a housing having an outer wall defining an exterior surface. A port opening to the passage is exteriorly accessible relative to the exterior face. With this in mind, the method includes providing a plurality of grooves in the exterior face of the outer wall such that the grooves are exteriorly open. Each groove extends from a trailing end to a leading end that is otherwise positioned proximate the port opening. A tip of the hypodermic needle is percutaneously directed toward the device and is located within one of the grooves at a point spaced from the corresponding leading end. The needle tip is tracked along the groove, toward the leading end thereof. In this regard, the groove within which the needle tip is located serves as a guide for directing the needle tip toward the port opening. Upon reaching the leading end of the groove in question, the needle tip is further moved beyond the groove and into the port opening for interfacing with the septum. In one embodiment, the method further includes initially piercing the patient's skin with the needle tip and contacting the needle tip against the housing's exterior face at a point between two of the grooves. Upon determining that the needle tip is not located within the groove, the user drags the needle tip across the exterior face, for example in a direction transverse to the expected port opening location. Movement of the needle tip continues until one of the grooves is encountered. Subsequently, the so-encountered groove is employed as a guide for directing the needle tip to the port opening, and thus the septum.

Yet other aspects in accordance with principles of the present invention relate to an implantable therapeutic substance delivery device for delivering a liquid therapeutic substance to a delivery site within a patient. The device includes a housing, a port assembly, and a plurality of guide means. The housing includes an outer wall forming an exterior face. The port assembly includes a port passage and a septum. The port passage terminates at a port opening that is exteriorly open relative to the exterior face. The septum is disposed across the passage. Finally, the plurality of guide means are discretely formed and are adapted for guiding a needle tip from a point spaced from the port opening to the port opening. In one embodiment, each of the guide means is a groove formed in the exterior face.

Yet other aspects in accordance with principles of the present invention relate to a method of manufacturing an implantable medical device for delivering a liquid therapeutic substance to a delivery site within a patient. The method includes providing a housing including an outer wall defining an exterior face. A port assembly is assembled to the housing. In this regard, the port assembly forms a passage and includes a septum disposed across the passage. Upon assembly to the housing, a port opening to the passage is defined, the port opening being exteriorly open relative to the exterior face of the housing. A plurality of grooves are formed in the exterior face proximate the port opening such that the grooves are open relative to an exterior of the housing. In some embodiments, the grooves are formed by etching or inscribing the housing wall.

DETAILED DESCRIPTION OF THE INVENTION

Figure 1:
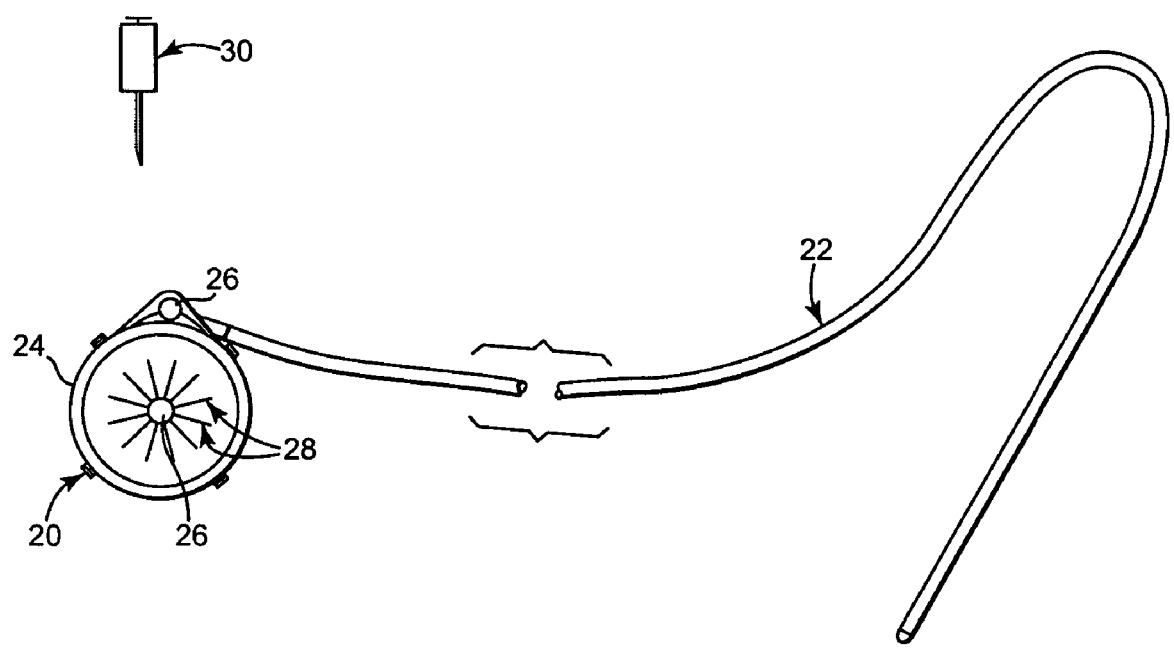
FIG. 1 is a top plan view of an implantable therapeutic substance delivery device including needle guide means in accordance with principles of the present invention, along with an implantable catheter and a needle.

One embodiment of an implantable therapeutic substance delivery device 20 in accordance with principles of the present invention is shown in FIG. 1, along with an implantable delivery catheter 22. In general terms, the delivery device 20, also known as a drug pump or medicament pump or device, can assume a variety of forms, and can be provided as part of an intrathecal system that further includes an external programmer (not shown). Regardless, the device 20 can be implanted below the skin of a patient, and operates to infuse a therapeutic substance (not shown) into the patient via the catheter 22 at a desired rate. In general terms, the delivery device 20 includes an outer housing 24 maintaining a reservoir (not shown) within which the therapeutic substance is contained, along with one or more port assemblies 26 (referenced generally). As described in greater detail below, the port(s) 26 can be provided to facilitate a variety of different applications, such as a reservoir refill port, catheter access port, etc. Regardless, the device 20 includes a plurality of needle guide means 28 (referenced generally) associated with at least one of the ports 26 adapted to assist a clinician in percutaneously directing a hypodermic needle 30 to the desired port 26.

Figure 2:
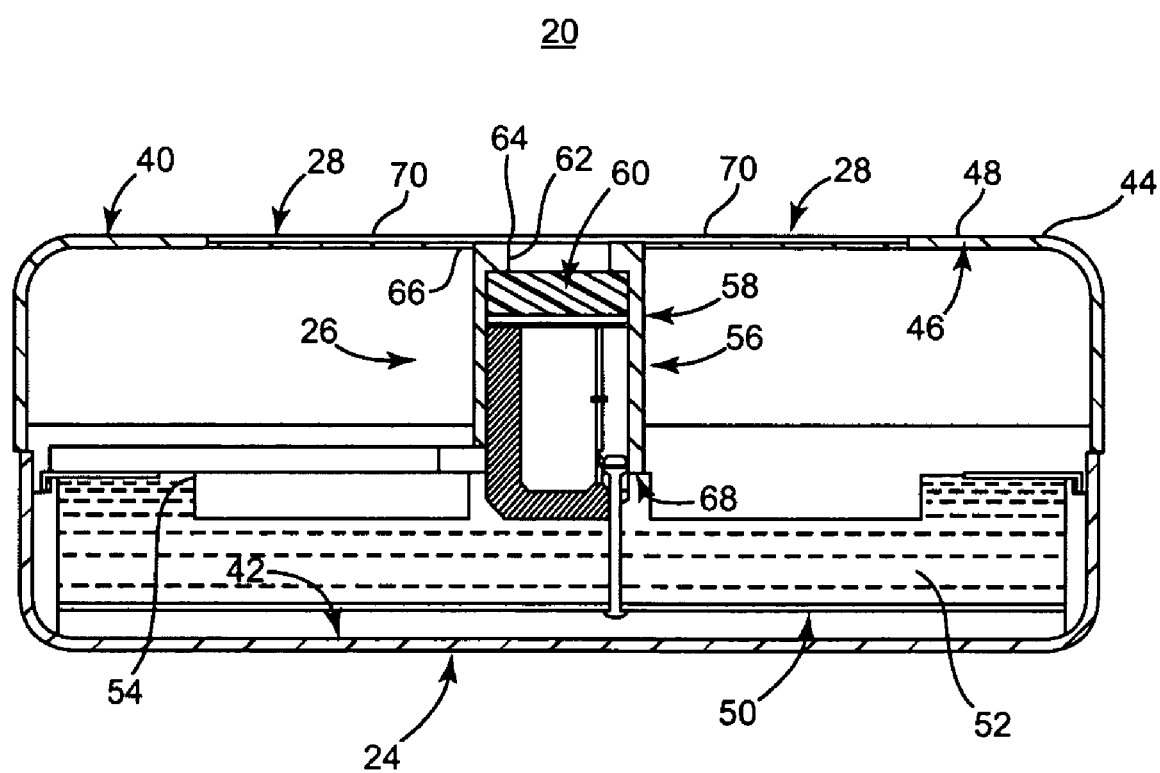
FIG. 2 is a simplified, cross-sectional view of the delivery device of FIG. 1.

A general construction of the implantable therapeutic substance delivery device 20 in accordance with some embodiments is shown in greater detail in FIG. 2. In particular, with the one embodiment of FIG. 2, the housing 24 includes first and second sections (sometimes referred to as "shields") 40, 42 that combine to define an exterior 44 (referenced generally) of the device 20. In this regard, each section 40, 42 includes a major wall (such as the major wall 46 of the first section 40) forming or defining an exterior face 48. In addition, the housing 24 maintains or forms a reservoir 50 otherwise containing (or filled or partially filled to contain) a desired liquid therapeutic substance 52 (illustrated generally). In this regard, the reservoir 50 can include or form a wide variety of structures or mechanisms useful to facilitate dispensement of the therapeutic substance 52 through an outlet 54 thereof, such as a bellows acted upon by a propellant as is known in the art. An additional pumping and/or metering mechanism (not shown) can also be provided to assist in directing flow of the therapeutic substance 52 from the reservoir outlet 54 to the catheter 22 (FIG. 1). As is known in the art, the therapeutic substance 52 is a product or substance intended to have a therapeutic effect, such as pharmaceutical compositions, genetic materials, biologics, and other substances. Other substances useful as the therapeutic substance 52 are intended to have a therapeutic effect yet are not easily classified such as saline solution, fluoroscopy agents, and the like.

The implantable therapeutic substance delivery device 20 can include additional components (such as a pumping and/or metering mechanism, electronics, power source, etc.) as known in the art. In this regard, the pumping mechanism can be, but is not limited to, a bladder pump, an accumulator pump, a fixed-rate bellows pump, etc. For example, in one embodiment, the delivery device 20 is akin to any implantable drug pump design known in the art such as the SynchroMed® EL infusion system available from Medtronic, Inc., of Minneapolis, Minn. Once again, a wide variety of other general device configurations are also envisioned, for example the IsoMed™ constant flow infusion system available from Medtronic, Inc., of Minneapolis, Minn.; the Paradigm® insulin pump available from Medtronic-MiniMed, Inc., of Northridge, Calif.; etc.

With the above conventions in mind, FIG. 2 further depicts one of the port assemblies 26, and in particular, a refill port assembly 56. The refill port assembly 56 provides a fluid connection to the reservoir 50 from an exterior of the device 20, and includes a port wall 58 and a septum 60. The port wall 58 can be formed in a variety of fashions and can be defined by one, two, or more separate structures. The port wall 58 defines a passage 62 that is accessible or open relative to an exterior of the housing 24 at a port opening 64. In some embodiments, the port opening 64 is defined directly by the housing 24. In other embodiments, the port wall 58 is formed apart from the housing 24, and is positioned within, and/or projects through, an aperture 66 in the housing outer wall 46 as shown. Regardless, the septum 60 is disposed within or across the passage 62 and is generally comprised of a resilient, resealable material, such as silicone rubber, which is durable enough to withstand numerous hypodermic needle punctures without leaking. With this configuration, then, the reservoir 50 can be percutaneously filled by inserting a needle (such as the hypodermic needle 30 of FIG. 1) through the patient's skin and then through the septum 60 via the port opening 64. Once the septum 60 has been pierced, the therapeutic substance 52 can be injected through the hypodermic needle 30 and into the reservoir 50. Though not shown, a similar port assembly can additionally be provided, establishing external fluid connection with the catheter 22 (FIG. 1), for example a catheter access port. Further, the refill port assembly 56 can include other components in some embodiments, such as a valve mechanism 68. Regardless, with the one embodiment of FIGS. 1 and 2, the plurality of needle guide means 28 are associated with the refill port assembly 56.

Figure 3A:
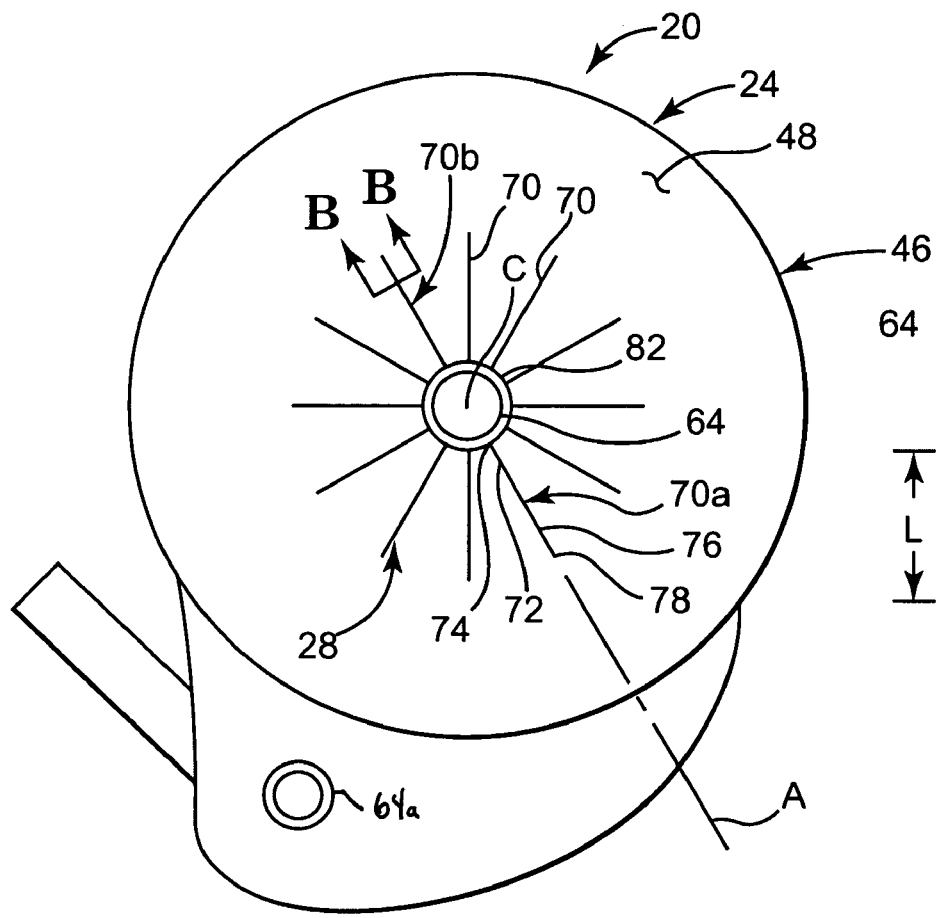
FIG. 3A is a top plan view of a portion of the delivery device of FIG. 1.

More particularly, and with additional reference to FIG. 3A, in one embodiment each of the needle guide means 28 comprises a groove or channel 70 (referenced generally) formed in the exterior face 48 of the housing wall 46 proximate the port opening 64. In one embodiment, the grooves 70 are discretely formed (for example are etched or machined into the exterior face 48), and at least several of the grooves 70 are equidistantly spaced relative to a circumference defined by the port opening 64. With this in mind, each of the grooves 70 (for example the groove 70a) is generally defined by a leading section 72 terminating at a leading end 74, and a trailing section 76 terminating at a trailing end 78. In one embodiment, the leading end 74 is formed or located proximate the port opening 64, whereas the trailing end 78 is spaced from the port opening 64. For example, the leading end 74 can terminate directly at (e.g., is open to) the port opening 64; in other embodiments, a slight spacing between the leading end 74 and the port opening 64 is defined. Regardless, the grooves 70 serve as guides for directing a needle (not shown) toward the port opening 64, and thus the port passage 62/septum 60.

For example, at least the leading section 72 of each of the grooves 70 is linear in extension relative to the port opening 64, defining a groove axis A. In some embodiments, an entirety of the groove 70 has a linear extension between the leading and trailing ends 74, 78. Regardless, the grooves 70 are formed or located such that the groove axis A of at least one, preferably all, of the grooves 70 approximately intersects a theoretic center point C defined by the port opening 64, and thus by the passage 62. Further, at least the leading section 72 of each of the grooves 70, and in some embodiments an entirety of each of the grooves 70, extends in a radial fashion relative to the center point C. With this configuration, then, each of the grooves 70 can guide a needle tip (not shown) toward the port opening 64.

While the plurality of needle guide means 28 are illustrated in FIG. 3A as including twelve discretely-formed grooves 70, in alternative embodiments, a greater or lesser number of the grooves 70 are provided. For example, the plurality of needle guide means 28 can include as few as four of the grooves 70. Alternatively, other numbers are also acceptable, such as eight, sixteen, twenty, twenty-four, etc., to name but a few.

In the one embodiment shown, the grooves 70 are equidistantly spaced relative to a circumference the port opening 64. In alternative embodiments, however, the grooves 70 need not be equidistantly spaced, and need not encircle an the port opening 64. More particularly, in one embodiment, grooves are not formed or otherwise present in areas that would otherwise constitute the groove extending from the port opening 64 toward other ports provided with the delivery device 20. For example, FIG. 3A illustrates an a catheter access port opening 64a (apart from the port opening 64). To avoid the possibility that a needle tip might unintentionally be directed toward the catheter access port opening 64a (instead of the port opening 64) via one of the grooves 70, in more some, more preferred embodiments, the delivery device 20 is configured such that there are no grooves extending from the port opening 64 toward the catheter port opening 64a (thus, for example, in some more preferred embodiments, the groove identified in FIG. 3A with the arrowhead from element number "28" would be eliminated). With this in mind, then, an arrangement or pattern of the grooves 70 can alternatively be described in terms of a spacing interval between adjacent grooves relative to the center point C of the port opening 64; in some embodiments at least three adjacent grooves define an equidistant spacing interval in the range of 10°-90°, more preferably approximately 15°-30°.

In one embodiment, at lest two, preferably all, of the grooves 70 are identical in terms of shape and size; although in other embodiments, one or more of the grooves 70 can have a different construction. For example, and with specific reference to FIG. 3A in which the grooves 70 have a linear extension from the leading end 74 to the trailing end 78, one or more of the grooves 70 can have a length L of at least 0.125 inch, preferably in the range of 0.125-1.0 inch, more preferably 0.375-0.75 inch. Similarly, and with reference to FIG. 3B, one or more of the grooves 70, such as the groove 70a, can have a width W in the range of 0.005-0.01 inch, more preferably 0.01-0.05 inch; and a depth D of at least 0.0005 inch, more preferably at least 0.001 inch, more preferably in the range of 0.003-0.025 inch (it being understood that where a thickness of the housing wall 46 is increased, the groove depth D can also be increased); although any other dimensions are also acceptable. With the one embodiment of FIG. 3B, the groove 70b has a triangular shape, with the width W being defined at the exterior face 48 of the housing wall 46. With this generally triangular shape, then, the groove 70a depth terminates at a point 80 opposite the exterior face 48. Alternatively, however, one or more of the grooves 70 can be formed to assume a variety of other shapes (e.g., square, rectangular, semi-circular, curvilinear, etc.) that may or may not be symmetrical. Regardless, the width W is sufficiently sized to receive a hypodermic needle (not shown) conventionally used with implantable therapeutic substance delivery devices, and the depth D is of sufficient magnitude so that the needle tip does not readily disengage from the groove 70 once positioned therein.

Figure 3B:
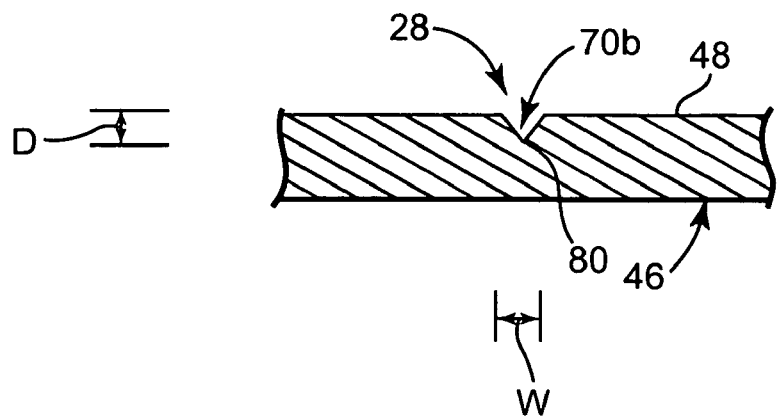
FIG. 3B is an enlarged, cross-sectional view of a portion of the device of FIG. 3A along the lines B-B.
Figure 3C:
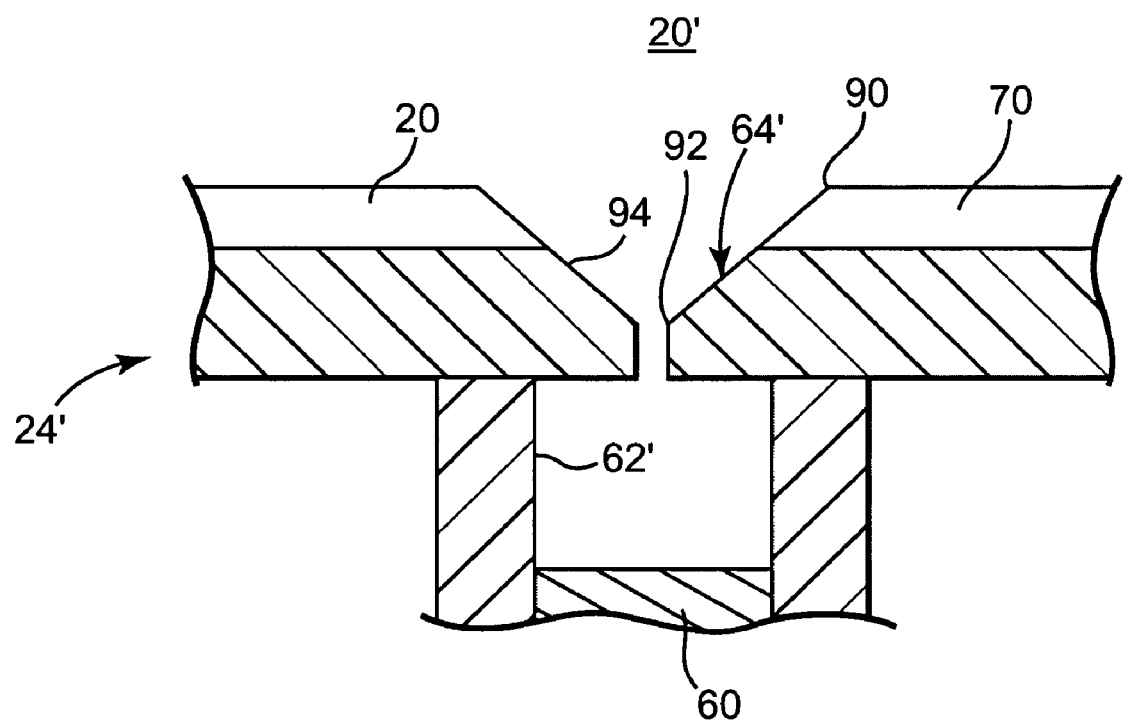
FIG. 3C is a simplified, cross-sectional view of a portion of an alternative embodiment implantable delivery device in accordance with principles of the present invention.

With the one embodiment of FIG. 3B, the exterior face 48 of the housing wall 46 is substantially flat in a region of the needle guide means 28. Further, and with additional reference to FIG. 3A, a perimeter 82 of the port opening 64 is substantially planar relative to portions of the exterior face 48 immediately adjacent the port opening 64. Along these same lines, the port opening 64 associated with the one embodiment of FIG. 2 terminates directly at the port wall 58. That is to say, the passage 62 of the port wall 58 (to which the septum 60 is otherwise secured) extends directly from the port opening 64. Alternatively, however, the housing 24/port opening 64 can assume a variety of other configurations. For example, the housing 24 can form a ring-like rib projecting outwardly from the exterior face 48 about the port opening 64 to provide a clinician with a surface for tactilely estimating the port opening 64 location through the patient's skin. Additionally, and with reference to FIG. 3C, otherwise illustrating components of an alternative embodiment implantable therapeutic substance delivery device 20', the housing 24' (and/or separate component such as a port wall provided apart from the outer housing 24') can form the port opening 64' as a conical depression. More particularly, the port opening 64' includes an outer perimeter 90, an inner perimeter 92, and a conical surface 94 extending therebetween. With this configuration, the grooves 70 (two of which are represented generally in FIG. 3C) terminate at or immediately adjacent the outer perimeter 90. As described in greater detail below, the grooves 70 provide a feature capable of guiding the needle tip (not shown) to the outer perimeter 90 of the port opening 64'; upon reaching the outer perimeter 90, the conical surface 94 serves to direct the needle tip to the inner perimeter 92 and thus into the port passage 62' and ultimately the septum 60.

Figure 4:
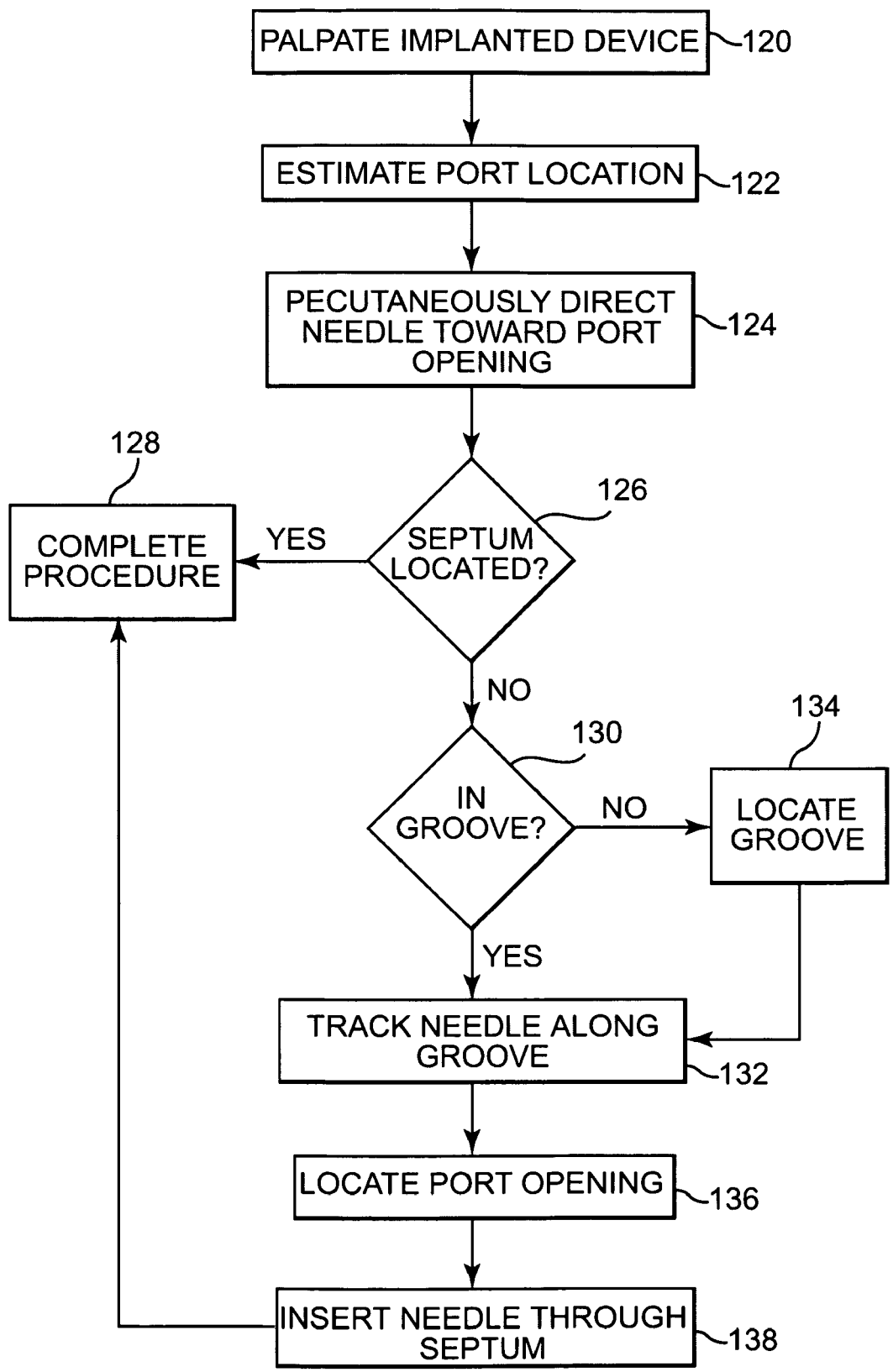
FIG. 4 is a flow diagram illustrating a method of percutaneously delivering a hypodermic needle to a septum associated with an implantable therapeutic substance delivery device.
Figure 5:
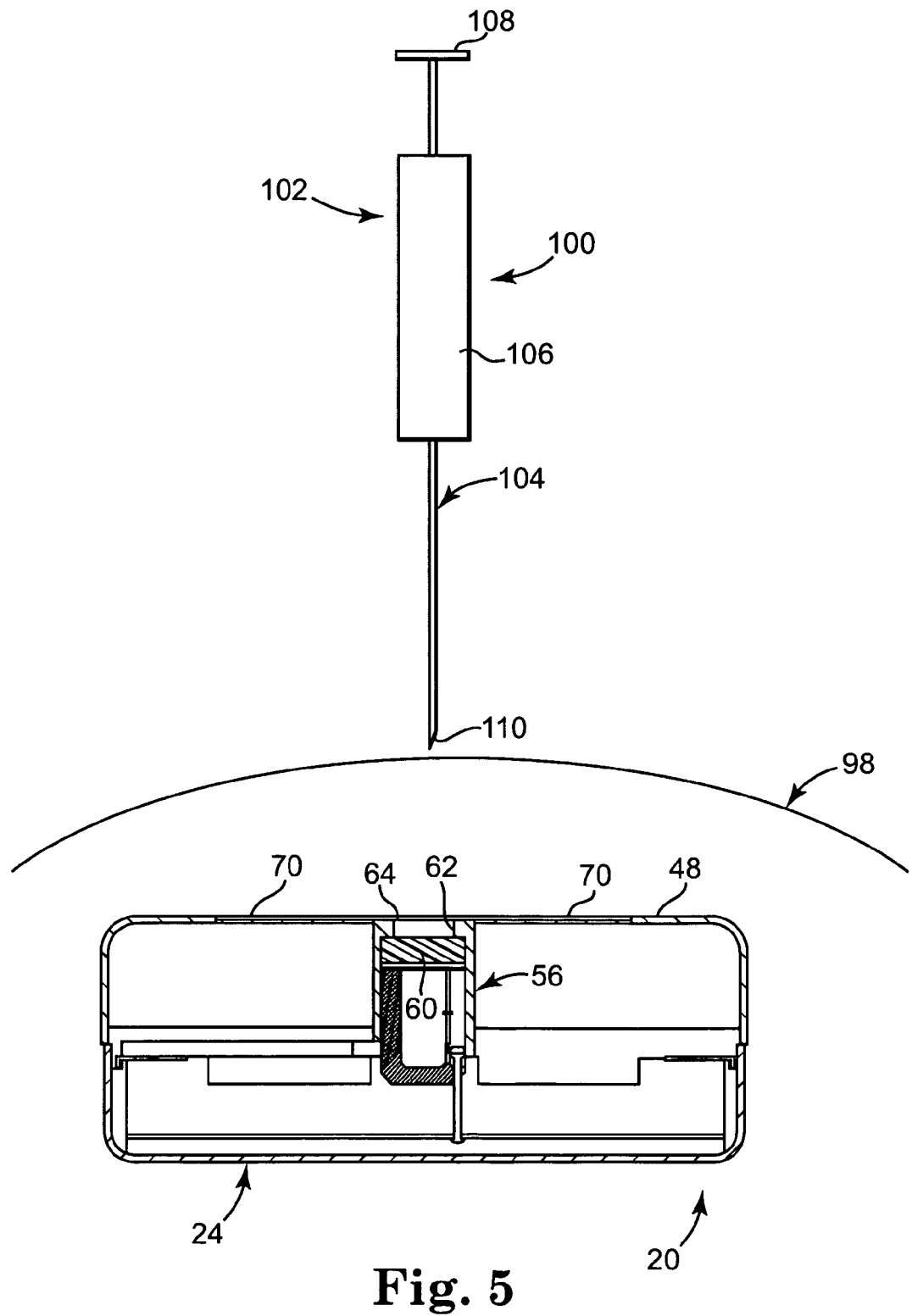
FIG. 5 is a simplified side view of the delivery device of FIG. 1 implanted within a patient, along with a syringe assembly.

Regardless of an exact configuration of the delivery device 20, 20', one method for percutaneously guiding a hypodermic needle to a septum associated with a human implantable therapeutic substance delivery device can be described with reference to the flow diagram of FIG. 4. In particular, and with additional reference to FIG. 5, following implantation of the delivery device 20 beneath a patient's skin 98, a clinician initially determines that a need exists to access a port assembly (such as the refill port assembly 56) using a hypodermic needle. As a point of reference, a hypodermic syringe assembly 100 is schematically illustrated in FIG. 5, and generally includes a handle portion 102 and a needle 104. The handle portion 102 generally includes a cylinder 106 and a plunger 108, whereas the needle 104 terminates at a needle tip 110. With this in mind, one method in accordance with principles of the present invention includes, at step 120, the clinician palpates the delivery device 20, and in particular a perimeter of the housing 24, through the patient's skin 98.

Once a general location and orientation of the housing 24 has been determined, the clinician estimates an approximate location of the port assembly of interest at step 122. In particular, and relative to the one embodiment in which the clinician desires to interface with the refill port assembly 56, the port opening 64 is generally located, such as via palpation/tactile feel and/or other auxiliary items such as a template.

Regardless, at step 124, the clinician manipulates the handle portion 102 of the hypodermic syringe assembly 100 to cause the needle tip 110 to pierce the patient's skin 98 at the estimated location of the port opening 64 (relative to the patient's skin 98), and percutaneously advances the needle tip 110 toward the estimated location of the port opening 64 at step 124. At step 126, based upon a sensed resistance to forward (or distal) movement of the needle tip 110, the clinician determines whether the needle tip 110 has been successfully positioned through the port opening 64 and thus into contact with the septum 60. If so, the method terminates at step 128 at which the clinician then operates the syringe assembly 100 (or other liquid delivery system) to perform/complete the desired activity (e.g., delivering a volume of therapeutic substance, withdrawing liquid, etc.).

Conversely, if the clinician determines that the needle tip 110 is not positioned within the port opening 64 (such as by the clinician sensing a hard stop to forward motion of the needle 104, otherwise indicative of the needle tip 110 contacting a surface other than the resilient septum, and in particular the housing 24), the clinician determines at step 130 whether the needle tip 110 has been initially positioned within one of the grooves 70. For example, the clinician can, by manually manipulating the handle portion 102, attempt to move or pivot the needle tip 110 back-and-forth and side-to-side (relative to the orientation of the handle portion 102 as held in the clinician's hand) a small distance. Under these circumstances, if the needle tip 110 is actually within one of the grooves 70, the clinician will sense a distinct resistance to one of the back-and-forth or side-to-side movements as the needle tip 110 otherwise bears against a side wall associated with the groove 70 within which the needle tip 110 is located.

Figure 6:
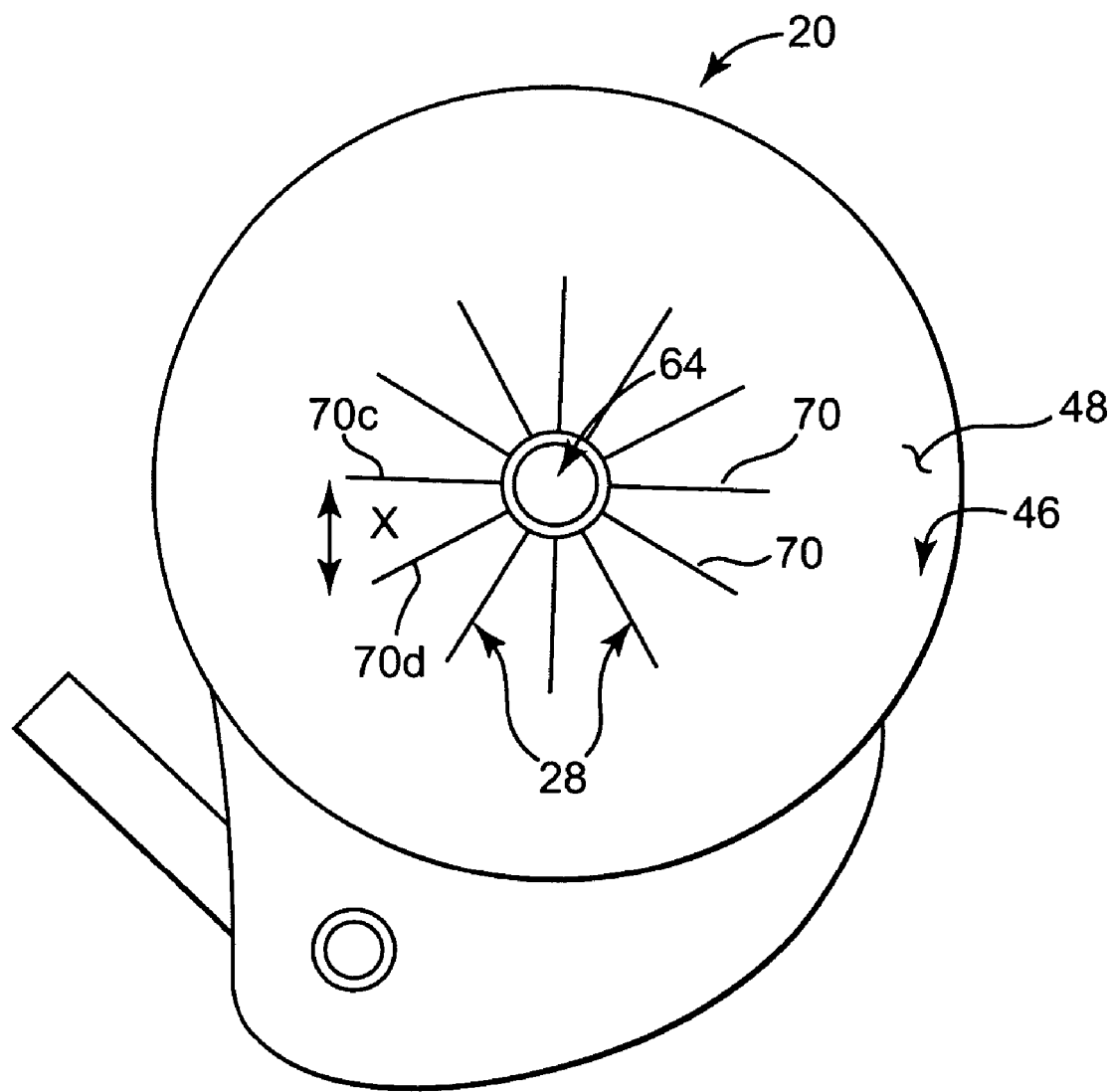
FIG. 6 is a top plan view of the delivery device of FIG. 1, illustrating a portion of the method of FIG. 4.

If, at step 130, the clinician determines that the needle tip 110 is disposed within one of the grooves 70, the method proceeds to step 132 as described below. Conversely, if it is determined that the needle tip 110 is not within one of the grooves 70 (e.g., the needle tip 110 freely moves side-to-side and back-and-forth), the method proceeds to step 134 at which the clinician moves the needle tip 110 along the exterior face 48 to locate one of the grooves 70 at step 134, by manipulating the handle portion 102. In this regard, the clinician can randomly move the needle tip 110 (again, by manually manipulating the handle portion 102) until a tactile sensation is recognized indicative of the needle tip 110 becoming engaged within one of the grooves 70. Alternatively, to more quickly locate one of the grooves 70, the clinician can be instructed to move the needle tip 110 in a direction generally perpendicular to the anticipated direction to which the needle tip 110 might otherwise need to be moved in order to encounter the port opening 64. By way of example, FIG. 6 illustrates a simplified, top plan view of a portion of the device 20, including the port opening 64 and the needle guide means 28 in the form of the grooves 70. With this in mind, a hypothetical, initial needle tip "stick" or point of contact against the exterior face 48 of the housing wall 46 is represented at the point "X". Under these circumstances, where the clinician estimates that the port opening 64 is likely located to the right (relative to the orientation of FIG. 6) of the initial contact point X, instead of moving the needle tip 110 (FIG. 5) in a rightward manner, the clinician is instead instructed to move the needle tip 110 perpendicular to the direction of estimated port opening location (i.e., up or down relative to the orientation of FIG. 6) as shown by arrows in FIG. 6. Pursuant to these guidelines, then, the needle tip 110 will readily encounter one of the grooves 70 adjacent the initial contact point X such as the groove 70c or 70d. Alternatively, the clinician can move the needle tip 110 in a variety of directions, virtually any one of which will cause the needle tip 110 to encounter one of the grooves 70.

Returning to FIGS. 4 and 5, upon locating the needle tip 110 within one of the grooves 70 (e.g., via a tactile evaluation by the clinician), at step 132 the clinician manipulates the handle portion 102 to cause the needle tip 110 to track along the engaged groove 70. Because each of the grooves 70 radiate inward to the port opening 64, tracking of the needle tip 110 within the groove 70 rapidly guides or directs the needle tip 110 to the port opening 64 at step 136. Subsequently at step 138, the needle tip 110 can then be inserted within the port passage 62, and pierced through the septum 60. Finally, the method proceeds to step 128 at which the syringe assembly 100 (or other liquid delivery system) is operated to complete the desired procedure. For example, the syringe assembly 100 can be operated to effectuate a reservoir refilling procedure.

The implantable therapeutic substance delivery device, and in particular the needle guide means and related method of use, of the present invention provides a marked improvement over previous designs. The grooves or other needle guide means provide a direct tactile feedback to the clinician as part of a percutaneous septum access procedure, enabling quick and accurate percutaneous location of the septum. Unlike prior designs, the clinician is no longer required to perform multiple needle sticks and/or randomly drag the needle tip over the device's exterior surface in hopes of locating the desired port assembly.

Although the present invention has been described with reference to preferred embodiments, workers skilled in the art will recognize that changes can be made in form and detail without departing from the spirit and scope of the present invention. For example, while the various embodiments described herein have described the needle guide means in conjunction with a reservoir refill port assembly, principles of the present invention can also be applied to other port assemblies, for example a catheter access port assembly. Further, the needle guide means in accordance with principles of the present invention can be applied to other types of implanted port assembly devices, such as a port for a drug dosage kit, that do not necessarily include a pumping mechanism.

What is claimed is:

1. An implantable medical device for delivering a liquid therapeutic substance to a delivery site within a patient, the device comprising:
    a housing including an outer wall defining an exterior face;
    a port assembly including a port passage terminating at a port opening that is exteriorly open relative to the exterior face, and a septum disposed across the port passage; and
    a plurality of grooves formed in the exterior face extending from the port opening, the plurality of grooves being open relative to the port opening and an exterior of the device, wherein the plurality of grooves are sized to receive a needle tip and each of the plurality of grooves has a width in the range of 0.01-0.05 inch.

2. The device of claim 1, wherein each of the grooves are configured and located to guide a needle tip positioned therein toward the port opening.

3. The device of claim 1, wherein each groove extends continuously between a leading end and a trailing end, the leading end of each groove being formed immediately adjacent the port opening and the trailing end being spaced from the port opening a distance greater than the leading end.

4. The device of claim 3, wherein each of the grooves includes a leading segment terminating in the leading end, and further wherein the leading segment is linear.

5. The device of claim 4, wherein an axis of each of the linear leading segments approximately intersects a center point of the port opening.

6. The device of claim 4, wherein an entirety of each of the grooves is linear.

7. The device of claim 1, wherein the port opening includes an outer perimeter, an inner perimeter, and a conical surface extending between the inner and outer perimeters, and further wherein each of the grooves terminates adjacent the outer perimeter.

8. The device of claim 1, wherein the port opening is defined by the exterior face of the housing.

9. The device of claim 1, wherein the port assembly further includes a port wall forming the port opening and passage, the port wall being assembled to an aperture in the exterior face.

10. The device of claim 1, wherein the plurality of grooves include at least four discrete grooves.

11. The device of claim 1, wherein the plurality of grooves includes at least twelve discrete grooves.

12. The device of claim 1, wherein each of the grooves are formed to extend in a radial fashion relative to a center point of the port opening.

13. The device of claim 1, wherein an equidistant spacing interval is defined between at least three adjacent grooves, the spacing interval being in the range of 15°-30°.

14. The device of claim 1, wherein at least two of the grooves have a length of at least 0.125 inch.

15. The device of claim 1, wherein at least two of the grooves have a depth of at least 0.001 inch.

16. The device of claim 1, wherein the housing maintains a reservoir for containing the liquid therapeutic substance, and further wherein the port assembly is fluidly connected to the reservoir such that the port assembly is a reservoir refill port assembly.

17. The device of claim 1, wherein the device further includes an implantable catheter fluidly connected to a reservoir otherwise containing the liquid therapeutic substance, the catheter adapted to deliver the therapeutic substance from the reservoir to a delivery site within the patient, and further wherein the port assembly is fluidly connected to the catheter such that the port assembly is a catheter access port assembly.

* * * * *